United States Patent
Otten (10) Patent No.: US 10,039,442 B2
(45) Date of Patent: Aug. 7, 2018

(54) ANTI-FOG FILM FOR AN ENDOSCOPE

(71) Applicant: Matthew Robert Otten, Cincinnati, OH (US)

(72) Inventor: Matthew Robert Otten, Cincinnati, OH (US)

(73) Assignee: SUR-SEAL CORPORATION, Cincinnati, OH (US)

( * ) Notice: Subject to any disclaimer, the term of this patent is extended or adjusted under 35 U.S.C. 154(b) by 505 days.

(21) Appl. No.: 14/592,292

(22) Filed: Jan. 8, 2015

(65) Prior Publication Data

US 2015/0223672 A1 Aug. 13, 2015

Related U.S. Application Data

(60) Provisional application No. 61/937,407, filed on Feb. 7, 2014.

(51) Int. Cl.
*A61B 1/00* (2006.01)
*A61B 1/253* (2006.01)
*A61B 1/04* (2006.01)

(52) U.S. Cl.
CPC ............ *A61B 1/253* (2013.01); *Y10T 29/4998* (2015.01)

(58) Field of Classification Search
CPC .............. A61B 1/0008; A61B 1/00089; Y10T 29/4998; Y10T 428/8305; G02B 27/0006
See application file for complete search history.

(56) References Cited

U.S. PATENT DOCUMENTS

| | | |
|---|---|---|
| 3,048,266 A | 8/1962 | Hackbel et al. |
| 4,307,004 A | 12/1981 | Schuhmacher et al. |
| 4,467,073 A | 8/1984 | Creasy |
| 4,551,484 A | 11/1985 | Rädisch et al. |
| 4,609,688 A | 9/1986 | Rädisch et al. |
| 4,872,878 A | 10/1989 | Tiffany |
| 5,324,573 A | 6/1994 | Evans |
| 5,359,453 A | 10/1994 | Ning |
| 5,392,766 A * | 2/1995 | Masterson ........... A61B 1/0008 15/244.1 |
| 5,412,504 A | 5/1995 | Leiner et al. |
| 5,476,682 A | 12/1995 | Evans |
| 5,549,543 A | 8/1996 | Kim |
| 5,575,756 A * | 11/1996 | Karasawa .......... A61B 1/00068 600/121 |
| 5,605,532 A | 2/1997 | Schermerhorn |

(Continued)

FOREIGN PATENT DOCUMENTS

| | | |
|---|---|---|
| WO | 2012112856 A1 | 8/2012 |
| WO | 2013013590 A1 | 1/2013 |
| WO | 2013049133 A1 | 4/2013 |

OTHER PUBLICATIONS

3M Medical Specialties Technical Bulletin: Frequently Asked Questions, "3M Hydrophilic Polyester Films for Diagnostics—No. 9960 and 9962", dated May 2008, downloaded from http://multimedia.3m.com/mws/media/ 797408O/technical-bulletin-faq-hydrophillic-films.pdf (4 pages).

(Continued)

*Primary Examiner* — Timothy J Neal (74) *Attorney, Agent, or Firm* — Daniel F. Nesbitt; Hasse & Nesbitt, LLC (57) ABSTRACT

An endoscope comprising a lens, and an anti-fog film, wherein an optically clear adhesive bonds the anti-fog film to the lens or lens section.

14 Claims, 7 Drawing Sheets

(56) References Cited

U.S. PATENT DOCUMENTS

| | | | |
|---|---|---|---|
| 5,954,637 | A | 9/1999 | Francis |
| 6,234,635 | B1 | 5/2001 | Seitzinger et al. |
| 6,455,142 | B1 | 9/2002 | Heberger et al. |
| 6,572,538 | B2 | 6/2003 | Takase |
| 6,712,479 | B1 | 3/2004 | Seitzinger et al. |
| 8,067,103 | B2 | 11/2011 | Hanson |
| 8,152,717 | B2 | 4/2012 | Gomez |
| 8,617,056 | B2 | 12/2013 | Haeckl et al. |
| 2006/0110578 | A1 | 5/2006 | Kikuchi et al. |
| 2006/0238870 | A1* | 10/2006 | Sneek ............... G02B 27/0006 359/512 |
| 2007/0077399 | A1 | 4/2007 | Borowiec et al. |
| 2007/0275344 | A1* | 11/2007 | Liu .................... A61C 19/004 433/29 |
| 2011/0051241 | A1 | 3/2011 | Ilvento |
| 2011/0216409 | A1 | 9/2011 | Stutes |
| 2013/0141693 | A1* | 6/2013 | McCabe ............... G02C 7/104 351/159.56 |

OTHER PUBLICATIONS

3M Technical Data: "3M Optically Clear Adhesives 8171CL and 8172CL", dated Feb. 2010, downloaded from http://multimedia.3m.com/ mws/media/631323O/3mtm-optically-clear-adhesive-8171cl-and-8172cl.pdf (4 pages).

* cited by examiner

ANTI-FOG FILM FOR AN ENDOSCOPE

CROSS-REFERENCE TO RELATED APPLICATIONS

This application claims the benefit of U.S. provisional application 61/937,407, filed Feb. 7, 2014, the disclosure of which is incorporated herein by reference.

FIELD OF THE INVENTION

This invention relates generally to an anti-fog lens for an endoscope. The invention also relates to methods of making an anti-fog lens for an endoscope.

BACKGROUND OF THE INVENTION

Foggy or blurry images on a video monitor or an eyepiece are a common cause of impaired vision during endoscopic surgery. One cause of a blurry image is fogging due to condensation on the lens. The condensation forms on the lens because the temperature of the lens is usually lower than body temperature. This causes dew point to be reached on the front surface of the lens, resulting in condensation on the lens. One procedure that may create fog is electrocauterization. Electrocauterization generates heat and water vapor, and the water vapor condensates on the typically cooler endoscope lens. What is needed is a device and method to reduce fogging of the lens due to condensation.

SUMMARY OF THE INVENTION

This invention relates to an endoscope comprising a lens, and anti-fog film, wherein an optically clear adhesive bonds the anti-fog film to the lens or lens section.

This invention also relates to an endoscope comprising a lens, and an anti-fog coating applied to the lens.

This invention further relates to a method of applying an anti-fog film to a lens of an endoscope comprising the steps of providing an anti-fog film, providing an optically clear adhesive, and adhering the anti-fog film to a lens with the optically clear adhesive.

This invention also relates to a method of fabricating a lens comprising the steps of providing a mold with a cavity for molding a lens, placing a film in the mold, the film having a first side, a second side, and an anti-fog coating applied to the second side, wherein the first side of the film faces the cavity of the mold, and injecting a material into the mold to mold a lens to the first side of the film.

DETAILED DESCRIPTION OF THE INVENTION

U.S. Pat. Nos. 4,964,710, 5,359,453, 5,412,504, 5,416,634, and 6,572,538 are incorporated by reference in their entirety.

Figure 1:
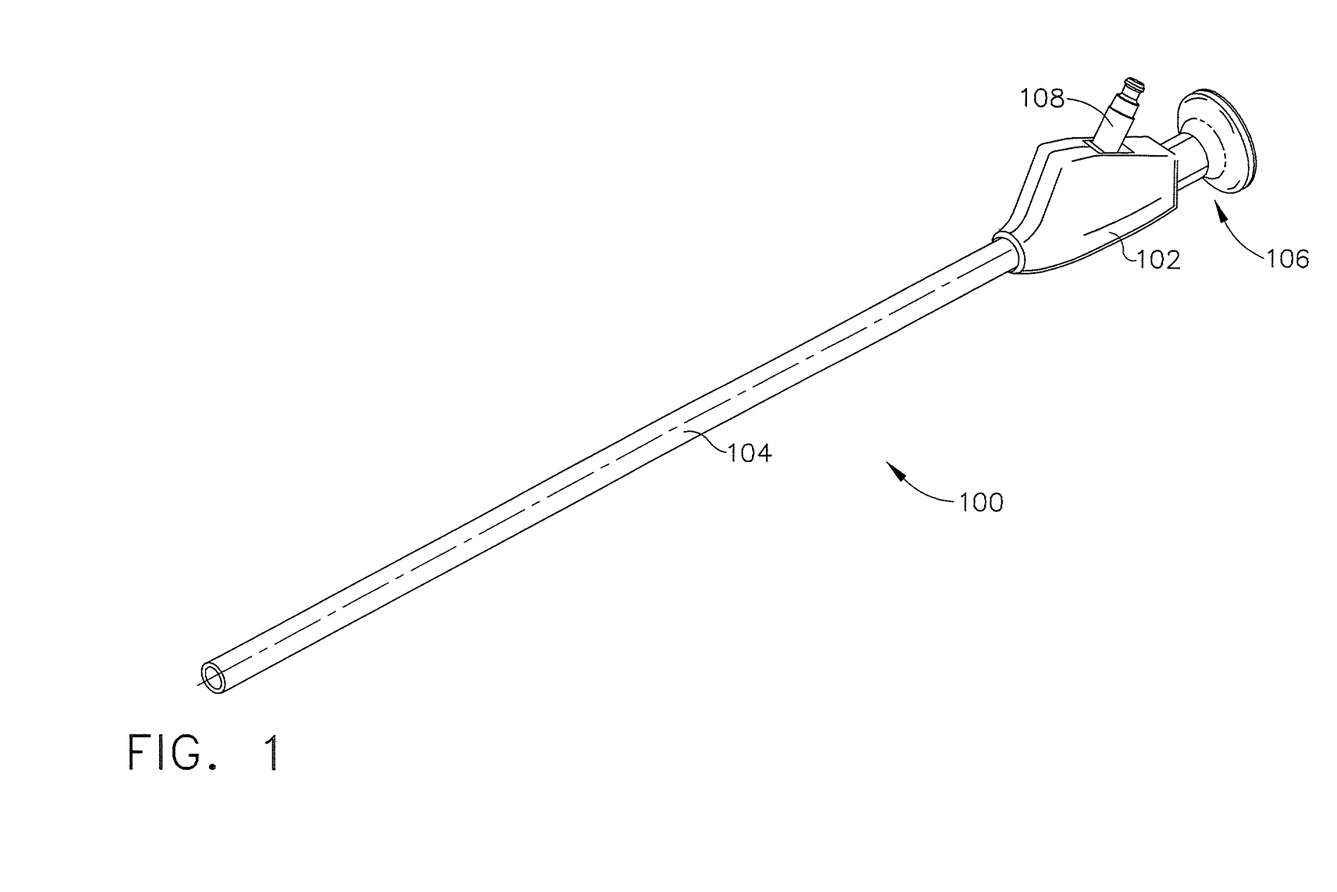
FIG. 1 shows an embodiment of an endoscope with an anti-fog film of the invention.

FIG. 1 shows a perspective view of an endoscope 100. One type of an endoscope is a laproscope for use in laparoscopic surgical procedures. Laparoscopic surgery is conducted in the peritoneal cavity of the patient involves insufflations of the peritoneal cavity with appropriate insufflations gases to raise the cavity wall, thereby permitting enhanced access to the internal organs within the cavity. Other types of endoscopes include arthroscopes, thoracoscopes, cystoscopes, hysteroscopes, laryngoscopes, gastroscopes, bronchoscopes and uteroscopes. As used in this application, endoscope encompasses those scopes and other scopes for surgical and diagnostic use.

Endoscope 100 includes housing 102 and a scope portion 104 extending from the housing 102. Housing 102 supports an eyepiece unit 106, which contains an eyelens assembly for viewing an image of an object formed by an optical system. Housing 102 also supports an illuminator connector 108. Illuminator connector 108 connects a conventional light guid which supplies illuminating light to the illumination system of the laparoscope.

Figure 2:
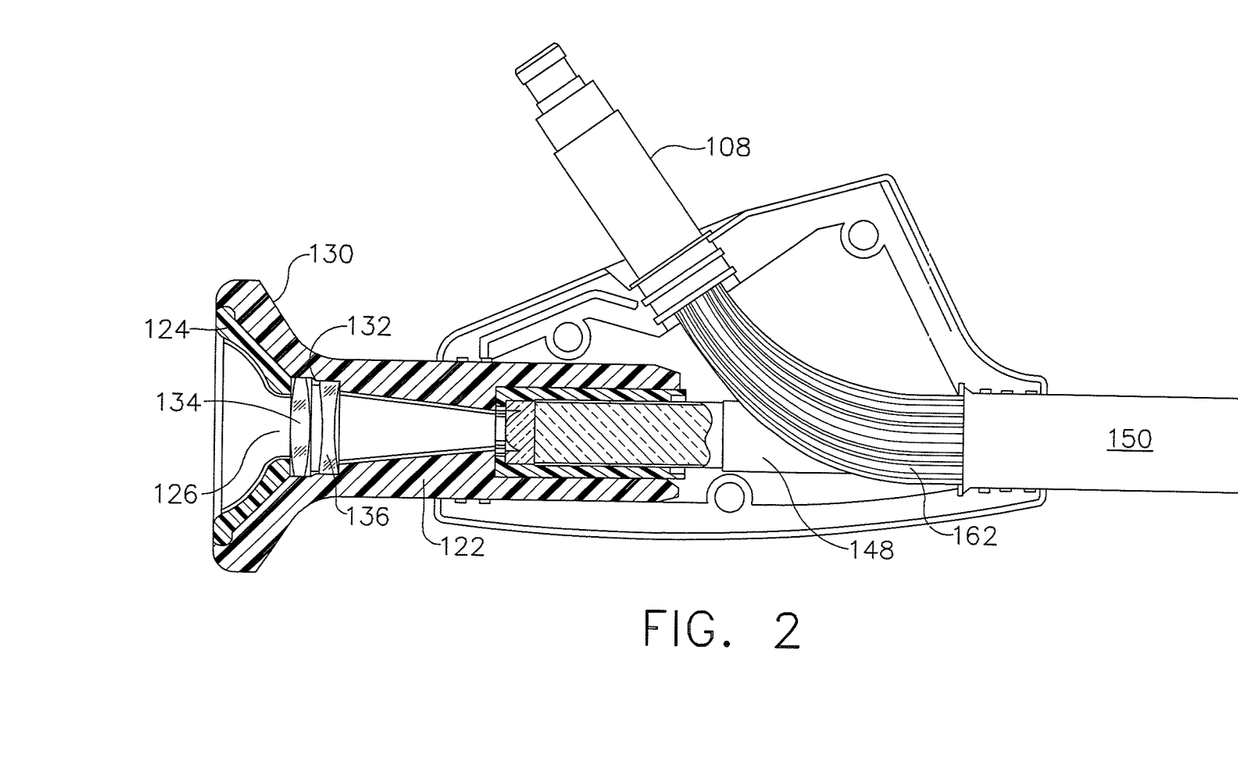
FIG. 2 shows an enlarged view of a housing of the endoscope of FIG. 1.

Referring to FIG. 2, eyepiece unit 106 includes eyepiece 122 and eyepiece cup 124 affixed to the proximal end face of the eyepiece 122. Eyepiece cup 124 includes a central aperture 126 to permit viewing of the image transferred by the optical system of the laparoscope.

An eyelens arrangement 132 is mounted within eyepiece 122. The eyelens arrangement provides a magnified image of the object transferred by the optical system and possesses two lenses 134, 136 mounted within the eyepiece. The eyelense arrangement 132 may be any conventional eyelense assembly.

Figure 3:
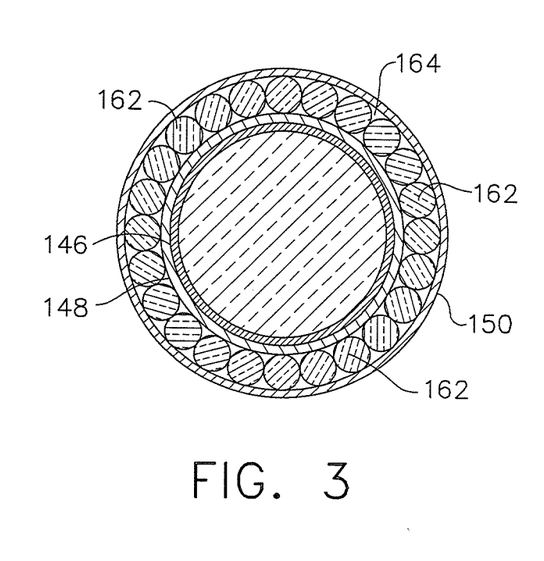
FIG. 3 shows a section view of an endoscope portion of the endoscope of FIG. 1.

Referring now to FIG. 3, a typical scope portion 104 defines a longitudinal axis 104a and consists of central optical lens tube 146 and inner and outer fiber tubes 148, 150, respectively. Optical lens tube 146 houses the optical components forming the objecting and relay lens arrangements of the optical system of endoscope 100.

Figure 3A:
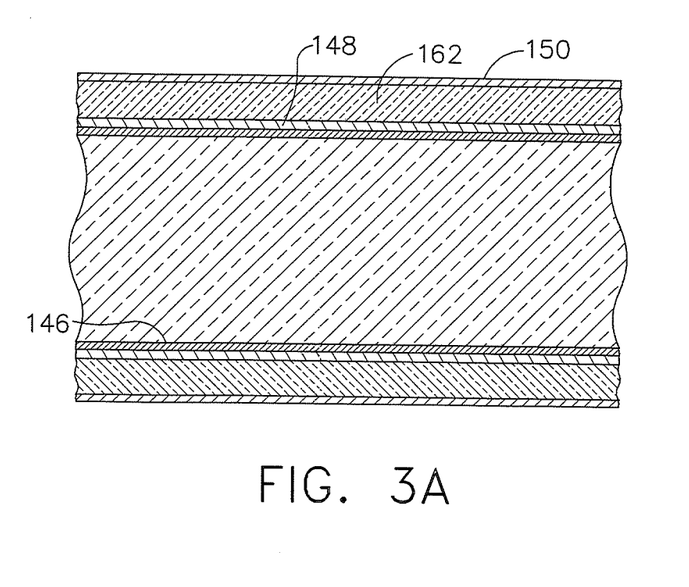
FIG. 3A shows a section view of the endoscope portion of FIG. 3.

The illumination system of endoscope 100 includes a plurality of optical fibers 162 extending within an annular space 164 defined between inner and outer lens fiber tubes 148, 150 thereby forming an annular array of the fibers 162 as depicted in FIG. 3A. The fibers 162 extend at their proximal ends within illuminating coupler 108. Optical fibers 162 may be fabricated from glass, polymeric materials, or other material sufficient to transfer the light. Optical fibers 162 define a diameter substantially equal to the distance between the inner and outer fiber tubes 148, 150. Generally, the objective lens arrangement forms an image of the object being viewed and the relay lens arrangement transfers the image through the endoscopic portion. Some optical systems that may be used are disclosed in U.S. Pat. Nos. 4,964,710, 5,359,453, 5,412,504, and 5,416,634. Other optical systems may also be used.

Figure 4:
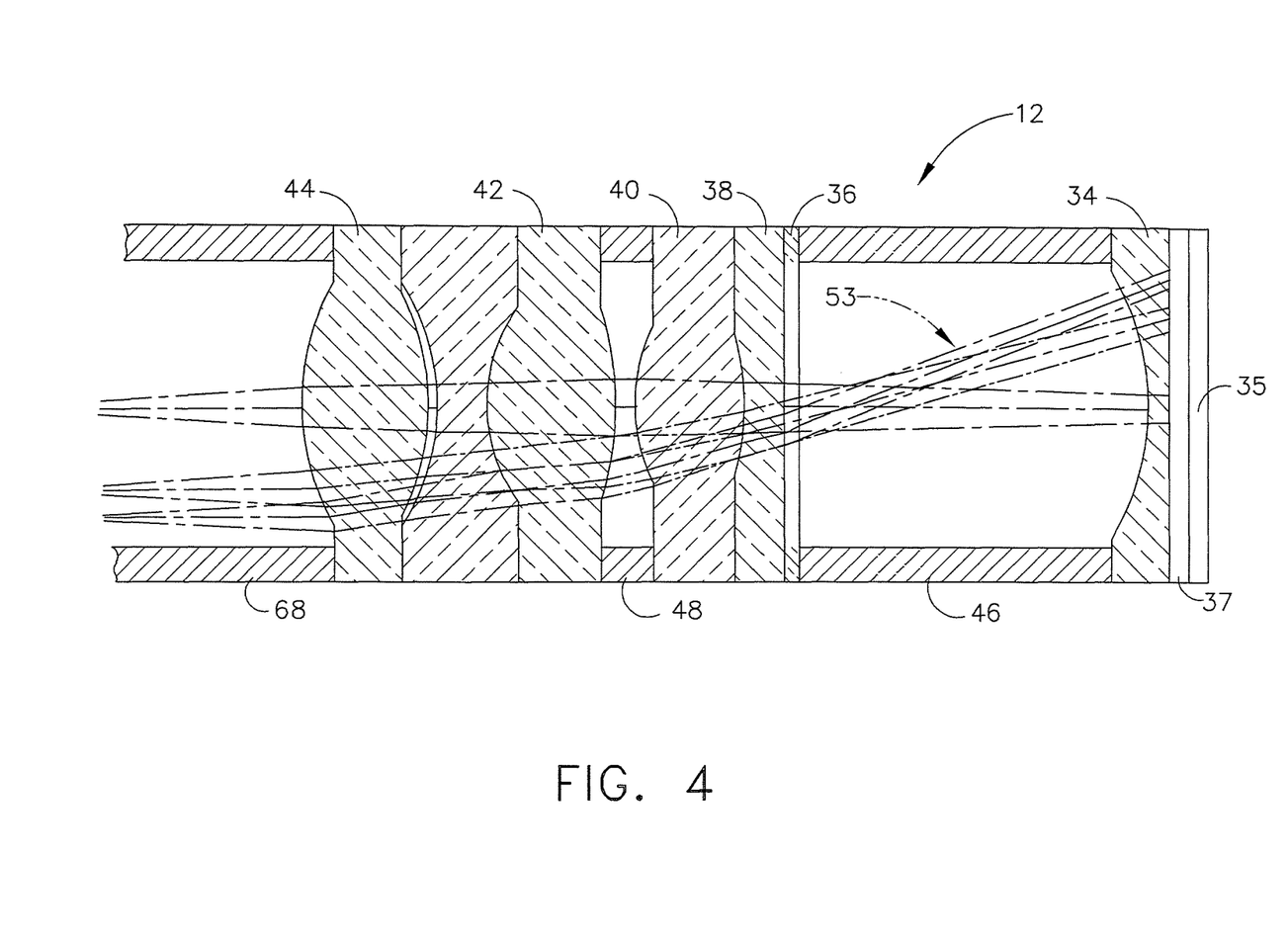
FIG. 4 shows an enlarged view of an objective lens section of the endoscope portion of FIG. 3.

FIG. 4 shows an objective lens section 12 that may be a part of a scope portion of an endoscope. The objective lens section 12 comprises lenses, including outer lens 34 and lenses 36, 38, 40, 42, and 44. An aperture stop may be located adjacent lens 38 and spacers 46, 48 may be used to locate the lenses. Each of the lenses 34-44 are typically plastic and may be made of any suitable optical material, including polymeric material, polymethylmethacrylate, polystyrene, polycarbonate, or silicone. Light 53 passes through the lens.

To prevent the outer lens 34 from fogging during procedures, it is covered with an anti-fog film 35. One example of an anti-fog film is 3M® Hydrophilic Polyester films for Diagnostics No. 9960 and 9962, which include a hydrophilic coating bonded to a polyester film. Other types of anti-fog films may also be used. Typically, hydrophilic coatings are used for anti-fog films. Hydrophilic films allow water to spread out, not head up on the surface of the film. The hydrophilic treatment which may be less than 1 micron thick may be bonded to a carrier film such as polyester.

To adhere the anti-fog film to the outer lens 34, an optically clear adhesive 37 is used. Here, optically clear adhesives are adhesives that do not substantially affect the quality of the image transmitted by the lens when applied in normal amounts to the lens. Typically, the optically clear adhesive is a removable adhesive to allow the anti-fog film to be removed before or during the time the endoscope is autoclaved or otherwise cleaned. Typically, the adhesive may have a refractive index of about 1.47. Haze, as measured according to ASTMD1003-92, is typically between 0.5% and 1%. Reflective-corrected total luminous transmission is typically greater than 99.5% across 380 nm to 780 nm wavelengths, when measured according to ASTM E903, D1003, and E284. More typically, the reflective-corrected total luminous transmission is greater than 99.75%.

In another embodiment, the anti-fog film may be applied to the lens during manufacturing. One method of applying an anti-fog film to the lens during manufacturing is to mold the anti-fog film to the lens. In another embodiment, an anti-fog coating is applied directly to the lens during manufacturing. Typically, when the coating is applied directly to the lens, the coating does not have a film carrier and may be less than 5 microns, and typically less than 1 micron thick.

Figure 5:
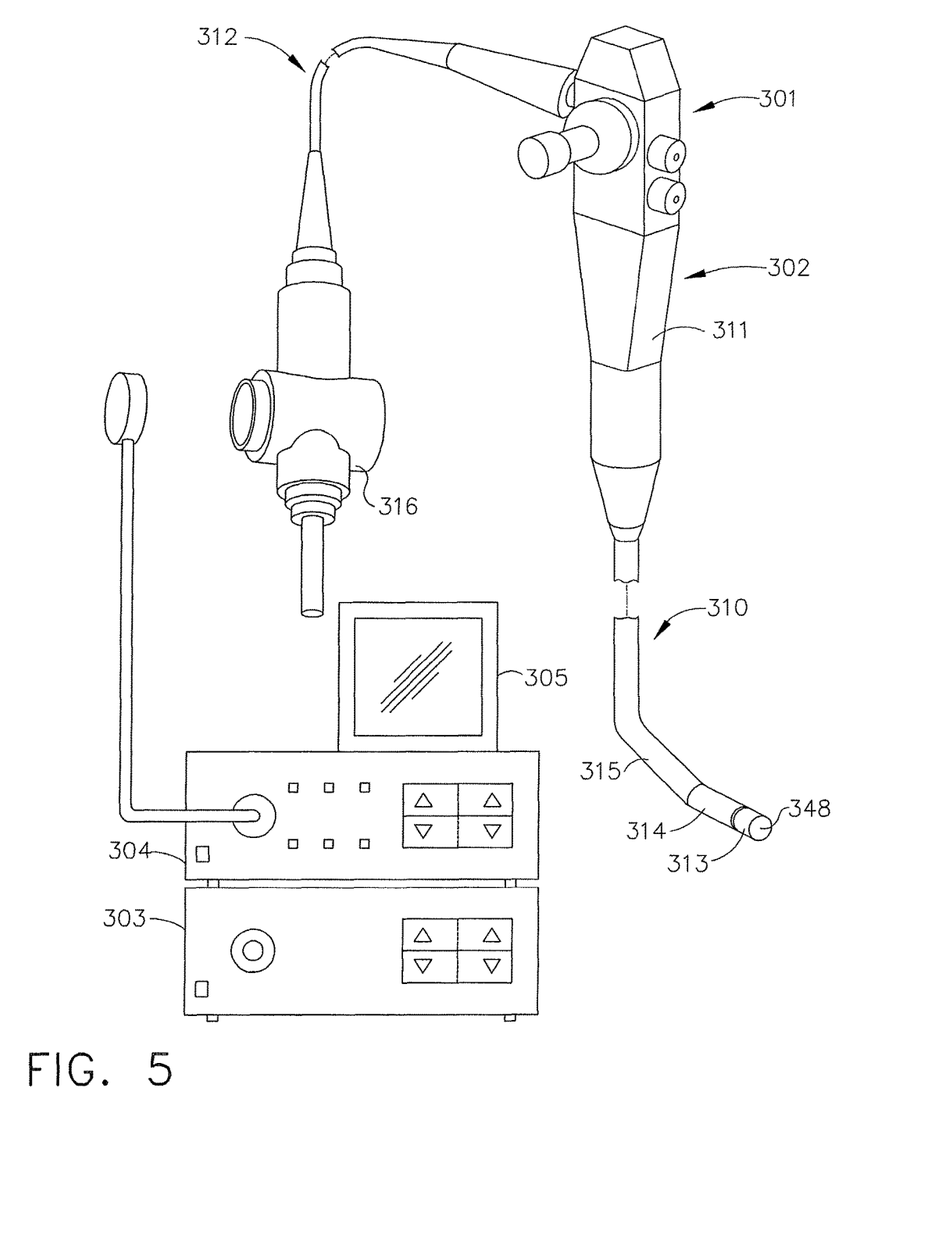
FIG. 5 shows another embodiment of an endoscope with an anti-fog film of the invention.

FIG. 5 shows another type of endoscope 301. The endoscope 301 has an electronic portion 302, a light source device 303, a video processor 304, and a monitor 305. The endoscope 301 has an imaging means, for which the light source device 303 provides light. The video processor 304 controls the imaging means as well as processing image signals obtained by the imaging means for video signals. The monitor 305 is connected to the video processor 304.

The endoscope 301 has an insertion member 310, a control member 311, and a universal cord 312. The insertion member 310 is elongated and flexible. The control section 311 is connected to the proximal end of the insertion member 310. The universal cord 312 is flexible, and is elongated from the side of the control section 311 to a connecting portion 316.

Figure 6A:
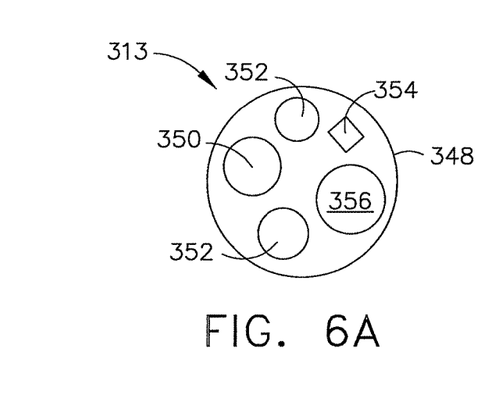
FIG. 6A shows face view of a distal end of the endoscope of FIG. 5.

The insertion member 310 of the endoscope 301 has a rigid part of distal end 313, a bending section 314, and a flexible tube 315 which is soft, and they are connected together. On the top face 348 of the rigid part 313, are placed for example, an observation window, an illumination window, and air and water supplying nozzle, and a suction port. Additionally, a biopsy channel or instrument channel, or both, may be included. FIG. 6A shows an example of the top face 348 of the distal end 313. The top face 348 has an image guide lens 350, at least one light guide lens 352, an air/water nozzle 354, and a channel 356 for doing a biopsy.

Figure 6B:
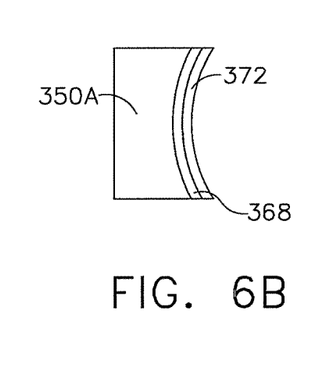
FIG. 6B shows a concave outer lens with an anti-fog film applied to it.
Figure 6C:
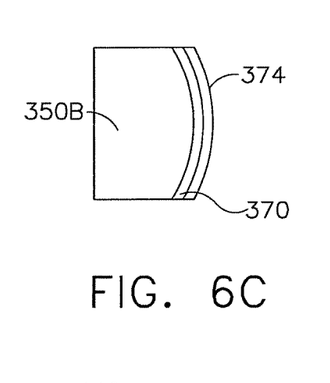
FIG. 6C shows a convex outer lens with an anti-fog film applied to it.

To prevent the image guiding lens 350 from fogging during procedures, it is covered with an anti-fog film. Anti-fog films and coatings like those described previously may be used. To adhere the anti-fog film to the image guiding lens 350, an optically clear adhesive is used. Typically, the optically clear adhesive is a removable adhesive to allow the anti-fog film to be removed before or during the time the endoscope is autoclaved or otherwise cleaned. Adhesives like those described previously may be used. The anti-fog film may be flat to adhere to a flat outer lens, as shown in 34, or it may be formed to fit a concave lens 350A as shown in FIG. 6B or convex lens as shown in FIG. 6C. FIG. 6B shows a concave lens 350A with an anti-fog film 372 applied to it with an adhesive 368. FIG. 6C shows a convex lens 350B with an anti-fog film 374 applied to it with an adhesive 370. Typically, the optically clear adhesive is a removable adhesive to allow the anti-fog film to be removed before or during the time the endoscope is autoclaved or otherwise cleaned.

Typically, the image guide lens 350 would be a convex lens 350B. As with the lens 34, the lenses 350, 350A, and 350B may be made of any suitable optical material, including optical polymeric material, including polymethylmethacrylate, polystyrene, polycarbonate, or silicone.

The adhesive may be preapplied to the anti-fog film. Similar to peal-and-stick labels, the user peals a backing from the anti-fog lens to expose the optically clear adhesive. The user then sticks the anti-fog film onto the lens. In another embodiment, the optically clear adhesive is applied with a brush or a sponge to the lens and the anti-fog film is placed on the lens. In another embodiment, the optically clear adhesive may be preapplied to the anti-fog film and provided in a roll similar to tape, in which the user pulls the anti-fog film from the roll, cuts off a section, and applies it to the lens.

To prevent air bubbles between the antifog film and the lens, a flexible scraper may be used to force any bubbles out from between the anti-fog film and the lens. If the lens is a flat lens, then a straight scraper may be used. If the lens is a convex lens or a concave lens, then a scraper with a notch matching the shape of the convex lens or a protrusion matching the shape of the concave lens may be used.

Figure 7:
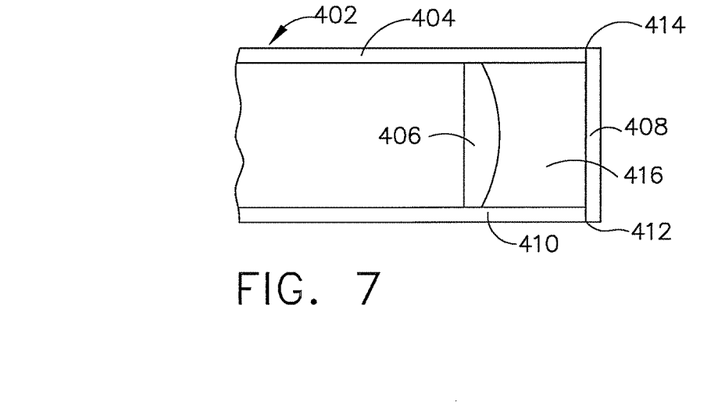
FIG. 7 shows an anti-fog film applied to an end of a scope extending beyond the lens.

The anti-fog film may also be applied to the end of the scope beyond the lens. FIG. 7 shows a lens section 402 having an optical lens tube 404, a lens 406, and an anti-fog film 408. The optical lens tube 404 has a distal portion 410 with an end 412 that extends beyond the lens 406. The anti-fog film 408 is adhered to the end 412 of the distal portion 410 of the lens tube 404. Typically, a seal 414 provided by an adhesive or other material used to adhere the anti-fog film 408 to the end 412 is a substantially vapor tight seal. As such, water vapor does not enter a space 416 between the lens 406 and the anti-fog film 408, thus preventing fogging of the lens.

The anti-fog film and the optically clear adhesive may also be absorbable. If the anti-fog film and optically clear adhesive are absorbable, then the body will absorb and degrade the anti-fog film and optically clear adhesive if the anti-fog film inadvertently dislodges from the lens during a procedure.

In another embodiment, the lenses 34, 350, 350A, 350B are made of silicone and have an anti-fog film or coating to prevent fogging. The silicone lens, or other type of lens material, may have an anti-fog film molded to the lens. The lens may be injection molded against a film with an anti-fog coating, a process typically known as co-molding.

Figure 8:
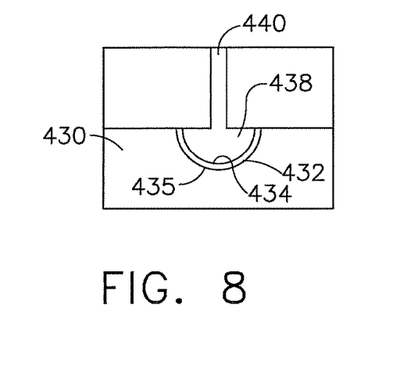
FIG. 8 shows a mold used to mold a lens against a film with an anti-fog coating.

FIG. 8 shows a mold 430 used for molding a lens against a film with an anti-fog coating. When fabricating an anti-fog lens by molding the lens against the anti-fog film, a film 432, having a first side 434 and a second side 435 with at least the second side having an anti-fog coating is placed in the mold. The mold has a cavity 438 for receiving lens material, and the film is placed so that the first side faces the cavity of the mold. The lens material is then placed in the cavity of the mold, typically using an injection molding technique to inject the lens material through a port 440, to mold the lens against the film. The material used to make the lens may be any suitable optical material, including silicone, polymeric material, polymethylmethacrylate, polystyrene, or polycarbonate.

Alternatively, an anti-fog coating may be applied directly to the lens. Typically, co-molding a lens to a film with an anti-fog coating and applying an anti-fog coating directly to the lens are completed during the manufacturing of the lens, rather than on-site at a medical facility.

Figure 9A:
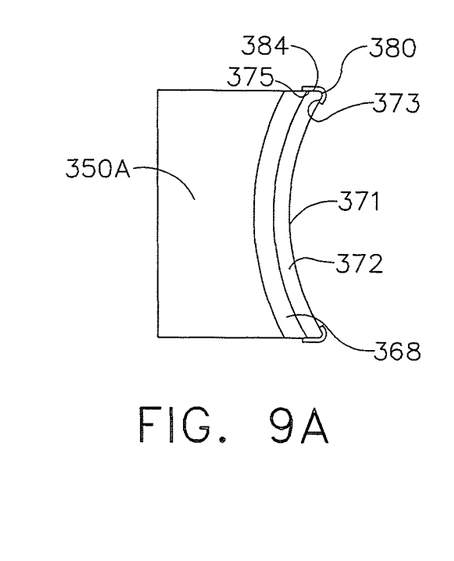
FIG. 9A shows the concave outer lens of FIG. 6B with a detectable element applied to the anti-fog film.
Figure 9B:
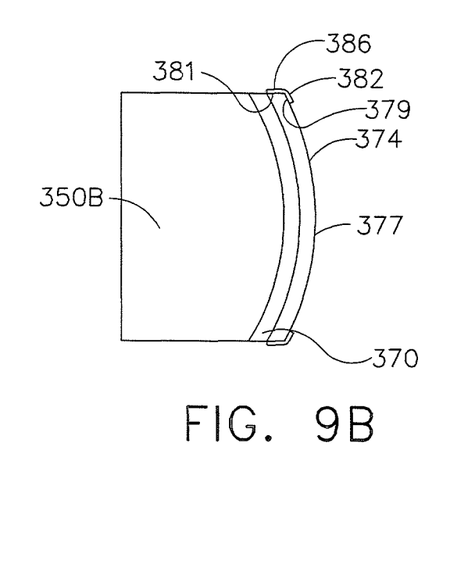
FIG. 9B shows the convex outer lens of FIG. 6C with a detectable element applied to the anti-fog film.

As shown in FIG. 9A, the anti-fog film 372 may have a detectable element 380 located on an outside face 371 of the anti-fog film 372. To avoid interfering with the optics, the detectable element 380 may be located at outer edge 373 of the anti-fog film 372. Alternatively, or in addition to the detectable element 380, the lens may have a detectable element 384 located on an outer perimeter 375 of the anti-fog film 372. As shown in FIG. 9B, the anti-fog film 374 may have a detectable element 382 located on an outside face 377 of the anti-fog film 374. To avoid interfering with the optics, the detectable element 382 may be located at outer edge 379 of the anti-fog film 374. Alternatively, or in addition to the detectable element 380, the lens may have a detectable element 386 located on an outer perimeter 381 of the anti-fog film 374. If an optically clear detectable element is used, then it may be placed at any location on the anti-fog film. The detectable element allows the anti-fog film to be detected by various means in the event it is dislodged from a lens during a patient procedure. Other anti-fog films, lenses, or materials may include a detectable element.

The detectable elements may be made of any one or more of various materials detectable by various methods. In one embodiment, the detectable element may be an opaque material that allows the anti-fog film to be seen by the naked eye. In another embodiment, the detectable element may be an opaque material detectable using the visualization capabilities of an endoscope. In another embodiment, the detectable element may be a material that fluoresces under a UV light. In another embodiment, the detectable material is a radio-opaque material that can be detected using x-rays. The radio-opaque material could be a metal, barium sulfate, ceramic, graphite, bismuth, or other appropriate radio-opaque material. The detectable element can deposited onto the film using printing, plating, painting, or other appropriate techniques. The detectable element can also be molded or formed into or on the anti-fog film.

While particular embodiments of the invention have been described, the invention can be further modified within the spirit and scope of this disclosure. This application is therefore intended to cover any variations, uses or adaptations of the invention using its general principles. Further, the application is intended to cover such departures from the present disclosure as come within known or customary practice in the art to which this invention pertains and which fall within the appended claims.

I claim:

1. A method of fabricating a lens for an endoscope having an anti-fog film with a detectable element that allows the anti-fog film to be detected in the event the anti-fog film is dislodged from the lens during use, comprising the steps of:
   (a) providing a mold with a cavity for molding a lens,
   (b) providing an anti-fog film having a first side and a second side, and comprising an anti-fog coating applied to the second side, and a detectable element applied to the anti-fog film,
   (c) placing the anti-fog film with the applied detectable element in the mold, with the first side of the anti-fog film facing the cavity of the mold, and
   (d) injecting a material into the mold to mold a lens to the first side of the anti-fog film.

2. The method according to claim 1, wherein the anti-fog coating is a hydrophilic coating.

3. The method according to claim 1, wherein the material is silicone.

4. The method according to claim 2, wherein the material is silicone.

5. The method according to claim 1, wherein the detectable element is applied on an outside face of the anti-fog film.

6. The method according to claim 5, wherein the detectable element is applied on an outer edge of the anti-fog film.

7. The method according to claim 6, wherein the detectable element is applied on an outer perimeter of the anti-fog film.

8. The method according to claim 7, wherein the detectable element is an opaque material and is visible by the naked eye.

9. The method according to claim 7, wherein the detectable element is a material that fluoresces under a UV light.

10. The method according to claim 7, wherein the detectable element is a radio-opaque material that can be detected using x-rays.

11. The method according to claim 10, wherein the radio-opaque material is selected from the group consisting of a metal, barium sulfate, ceramic, graphite, and bismuth.

12. The method according to claim 7, wherein detectable element is applied onto the anti-fog film using a method selected from the group consisting of printing, plating, and painting.

13. The method according to claim 7, wherein detectable element is applied by molding or faulting into or onto the anti-fog film.

14. The method according to claim 7, wherein applying the detectable element at the outer edge of the anti-fog film avoids interfering with the optics of the lens.

* * * * *

UNITED STATES PATENT AND TRADEMARK OFFICE
CERTIFICATE OF CORRECTION

| | |
|---|---|
| PATENT NO. | : 10,039,442 B2 |
| APPLICATION NO. | : 14/592292 |
| DATED | : August 7, 2018 |
| INVENTOR(S) | : Matthew R. Otten |

Page 1 of 1

It is certified that error appears in the above-identified patent and that said Letters Patent is hereby corrected as shown below:

In the Claims

In Column 6, Claim 13, Line 56, delete "faulting" and insert --forming--.

Signed and Sealed this
Ninth Day of October, 2018

Andrei Iancu
*Director of the United States Patent and Trademark Office*